United States Patent [19]

Richardson et al.

[11] Patent Number: 4,616,026
[45] Date of Patent: * Oct. 7, 1986

[54] ANTIFUNGAL 2-ARYL-1,1-DIFLUORO-3-(1H-1,2,4-TRIAZOL-1-YL)2-PROPANOLS

[75] Inventors: Kenneth Richardson; Peter J. Whittle, both of Canterbury, England

[73] Assignee: Pfizer Inc., New York, N.Y.

[*] Notice: The portion of the term of this patent subsequent to Nov. 20, 2001 has been disclaimed.

[21] Appl. No.: 517,175

[22] Filed: Jul. 25, 1983

[30] Foreign Application Priority Data

Feb. 16, 1983 [GB] United Kingdom ............... 8304282

[51] Int. Cl.⁴ ................ A01N 43/653; A01N 43/713; C07D 249/08; C07D 403/06
[52] U.S. Cl. ................................ 514/381; 260/665 R; 260/665 G; 514/383; 546/268; 546/276; 548/252; 548/262; 549/563; 556/415; 562/496
[58] Field of Search ............... 548/252, 262; 546/276, 546/278; 424/269, 263; 514/383, 381

[56] References Cited

U.S. PATENT DOCUMENTS

| 4,243,405 | 1/1981 | Balasubramanyan et al. ...... 424/245 |
| 4,386,088 | 5/1983 | Knanz et al. ........................ 424/269 |
| 4,483,863 | 11/1984 | Richardson et al. ............... 548/101 |

FOREIGN PATENT DOCUMENTS

| 15756 | 9/1980 | European Pat. Off. ............ 548/262 |
| 0031911 | 7/1981 | European Pat. Off. ............ 548/262 |
| 47594 | 3/1982 | European Pat. Off. ............ 548/262 |
| 48548 | 3/1982 | European Pat. Off. ............ 424/269 |
| 69442 | 1/1983 | European Pat. Off. ............ 548/262 |

OTHER PUBLICATIONS

Burger, Medicinal Chemistry, (Second Edition, New York, 1960), p. 1055, RS 403B8.

*Primary Examiner*—Alton D. Rollins
*Attorney, Agent, or Firm*—Charles J. Knuth; Albert E. Frost; Paul D. Thomas

[57] ABSTRACT

Compounds of the formula

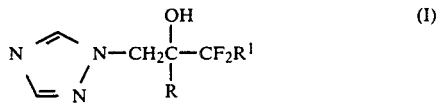

a pharmaceutically or agriculturally acceptable acid addition salt thereof wherein R is 5-chloro-2-pyridyl, phenyl or phenyl substituted by from 1 to 3 substituents, each independently selected from F, Cl, Br, I, $CF_3$, $(C_1-C_4)$alkyl and $(C_1-C_4)$alkoxy; and $R^1$ is H, Cl, phenyl, phenyl substituted by from 1 to 3 substituents each independently selected from F, Cl, Br, I and $CF_3$ or a heterocyclic group linked to the adjacent $CF_2$ group by a ring carbon atom; method for their use in combatting fungal infections in plants, seeds and animals, including humans, and pharmaceutical and agricultural compositions containing them.

9 Claims, No Drawings

ANTIFUNGAL 2-ARYL-1,1-DIFLUORO-3-(1H-1,2,4-TRIAZOL-1-YL)2-PROPANOLS

BACKGROUND OF THE INVENTION

This invention relates to novel triazole derivatives having antifungal activity which are useful in the treatment of fungal infections in animals, including humans, and as agricultural fungicides.

Published European Patent Application Nos. 15,756; 47,594 and 48,548 disclose triazole compounds of the formula

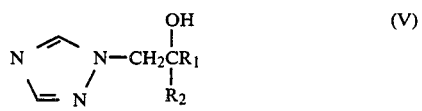

wherein $R_1$ is alkyl, cycloalkyl or optionally substituted phenyl and $R_2$ is phenyl or benzyl, each of which is optionally substituted, e.g. with halogen; methods for their use as plant fungicides and plant growth regulators, and pharmaceutical and veterinary compositions containing them.

Published European Patent Application No. 69,442 discloses difluorophenyl-1,3-bis-triazolylpropan-2-ol having antifungal activity.

SUMMARY OF THE INVENTION

According to the invention, there are provided compounds of the formula

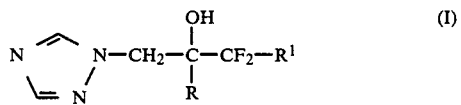

their O-esters and O-ethers, where R is 5-chloro-2-pyridyl, phenyl or phenyl substituted by 1 to 3 substituents each independently selected from F, Cl, Br, I, trifluoromethyl, ($C_1$–$C_4$)alkyl and ($C_1$–$C_4$)alkoxy; and $R^1$ is H, Cl, phenyl or phenyl substituted by 1 to 3 substituents each independently selected from F, Cl, Br, I and trifluoromethyl or a heterocyclic group linked to the adjacent $CF_2$ group by a ring carbon atom; or a pharmaceutically acceptable acid addition salt thereof.

The invention also provides a pharmaceutical composition comprising an antifungal amount of a compound of the formula (I) or an O-ester, O-ether or pharmaceutically acceptable acid addition salt thereof, together with a pharmaceutically acceptable diluent or carrier.

The invention further provides a compound of the formula (I) or an O-ester, O-ether or pharmaceutically acceptable acid addition salt thereof, for use in treating fungal infections in animals, including humans.

The invention also includes an agricultural composition suitable for use on a plant or seed comprising an antifungal amount of a compound of formula (I), an O-ester, O-ether or agriculturally acceptable acid addition salt thereof, together with an agriculturally acceptable diluent or carrier.

Yet further, the invention provides a method of treating an animal, including a human being, having a fungal infection, which comprises administering to the animal an antifungal effective amount of a compound of the formula (I), or an O-ester, O-ether or pharmaceutically acceptable acid addition salt thereof.

The invention also includes a method of treating a seed or plant having a fungal infection, which comprises administering to the plant or seed, or to the locus of said plant, an antifungally effective amount of a compound of the formula (I) or of an agriculturally acceptable acid addition salt thereof.

When R is said optionally substituted phenyl group, it is preferably trifluoromethylphenyl or phenyl substituted by 1 to 3 substituents, more preferably 1 or 2 substituents, each independently selected from F, Cl, Br and I. Particularly preferred values of R include 4-fluorophenyl, 4-chlorophenyl, 4-bromophenyl, 4-iodophenyl, 4-trifluoromethylphenyl, 2-chloro-4-fluorophenyl, 2,4-dichlorophenyl, 2,4-difluorophenyl, 2,4,6-trifluorophenyl and 4-bromo-2,5-difluorophenyl.

R is most preferably 4-fluorophenyl or 2,4-difluorophenyl.

When $R^1$ is a heterocyclic group it is preferably a 1,2,4-triazol-3-yl; 1-methyl-1,2,4-triazol-3-yl; 2-methyl-1,2,4-triazol-3-yl; 4-methyl-1,2,4-triazol-3-yl; imidazol-2-yl; 1-methyl-imidazol-2-yl or most preferably a 1-methyltetrazol-5-yl group.

$R^1$ is most preferably 4-fluorophenyl.

The O-ethers of the compounds of the formula (I) include, for example, the ($C_1$–$C_6$)alkyl, ($C_2$–$C_4$ alkenyl)methyl, ($C_2$–$C_4$ alkynyl)methyl, aryl (e.g. phenyl) and aralkyl (e.g. benzyl) optionally ring substituted by halo, ($C_1$–$C_4$)alkyl or ($C_1$–$C_4$)alkoxy ethers.

The O-esters of the compounds of the formula (I) include, for example, the ($C_2$–$C_4$)alkanoyl and aroyl (e.g. benzoyl), optionally substituted by halo, $C_1$–$C_4$ alkyl or ($C_1$–$C_4$)alkoxy esters.

The preferred O-ester is the acetate.

Especially preferred invention compounds include:
1,1-difluoro-1,2-bis-(4-fluorophenyl)-3-(1H-1,2,4-triazol-1-yl)propan-2-ol;
1-chloro-2-(2,4-difluorophenyl)-1,1-difluoro-3-(1H-1,2,4-triazol-1-yl)propan-2-ol; and
1,1-difluoro-2-(2,4-difluorophenyl)-3-(1H-1,2,4-triazol-1-yl)propan-2-ol.

DETAILED DESCRIPTION OF THE INVENTION

The compounds of formula (I) are prepared, for example, by reacting an oxirane of the formula

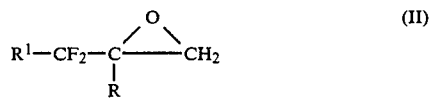

where R and $R^1$ are as defined for formula (I), with 1,2,4-triazole, preferably in the presence of a base, e.g. $K_2CO_3$. Alternatively an alkali metal salt of 1,2,4-triazole can be used, prepared e.g. from the triazole and sodium hydride. Typically the reaction is carried out by heating the reactants together at a temperature of from about 50° to 120° C. in a suitable organic solvent, e.g. dimethylformamide, for up to about 24 hours. The product can then be isolated and purified conventionally, e.g. as described in the Examples.

The oxiranes (II) are obtained by conventional methods, e.g. from the ketones of the formula:

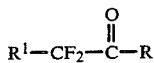

wherein R and $R^1$ are as previously defined. This can be achieved by the reaction of the starting ketone (III) with dimethyloxosulphonium methylide prepared from trimethylsulphoxonium iodide and either (a) sodium hydride in dimethylsulphoxide, or (b) cetrimide (cetyl-trimethylammonium bromide) and sodium hydroxide in a mixture of water and toluene or water and 1,1,1-trichloroethane. The reaction using sodium hydride is typically carried out by stirring approximately equimolar amounts of sodium hydride and trimethylsulphoxonium iodide at about room temperature. A molar excess of dimethylsulphoxide (DMSO) is then added dropwise and the mixture stirred for about 30 minutes, after which time the ketone (III) is added in DMSO. The desired product is generally obtained by stirring at room temperature for about an hour. The reaction using cetrimide is typically achieved by stirring the ketone (III), trimethylsulphoxonium iodide and cetrimide in a mixture of 1,1,1-trichloroethane and aqueous sodium hydroxide solution for about two hours at about 70°–100° C. While, in either case, the oxirane product (II) can be isolated if desired, it is often more convenient to convert this in situ to the desired product.

The ketones (III) are either known compounds or can be prepared by conventional procedures in accordance with literature precedents. Thus, for example, the ketone of formula (III) wherein $R^1$ is H and R is 2,4-difluorophenyl can be prepared by reacting 2,4-difluorobromobenzene with n-butyl lithium followed by reaction with difluoroacetic acid. Compounds wherein $R^1$ is chloro are prepared, for example, by reacting the appropriate substituted bromobenzene with magnesium to generate the Grignard reagent which is then reacted with chlorodifluoroacetic anhydride. Alternatively, ketones of the formula (III) where $R^1$ is phenyl or substituted phenyl may be prepared by reacting the Grignard reagent with the N-methoxy-N-methylamide of the appropriate acid $R_1CF_2-CO_2H$, prepared according to the procedure of Nahm and Weinreb described in Tetrahedron Letters, 22, 3815 (1981). Ketones of formula (III) wherein $R^1$ is a heterocyclic group are prepared from the corresponding 2-heterocyclyl-acetophenones by reacting with perchlorylfluoride. The procedures involved are well known to those skilled in the art as are the conditions for their performance and procedures for isolating, and if necessary purifying the products.

The requisite alpha, alpha-difluoroarylacetic acids are prepared from the corresponding alpha-oxoarylacetates by reaction with diethylaminosulfur trifluoride by the procedure of Middleton and Bingham, J. Org. Chem., 45, 2883 (1980).

The O-ethers can be made conventionally, e.g. by treating an alkali metal salt of a compound of the formula (I), e.g. a lithium or sodium salt, with the appropriate halide, e.g. an alkyl, alkenylmethyl, alkynylmethyl or aralkyl halide. O-Esters can be made by treating an alkali metal salt of compound (I) with the appropriate acid chloride, bromide or anhydride.

The compounds of the invention contain an optically active center and the invention includes both the resolved and unresolved forms.

Pharmaceutically acceptable and agriculturally acceptable acid addition salts of the compounds of the formula (I) are those formed from strong acids which form non-toxic acid addition salts, such as hydrochloric, hydrobromic, sulphuric, oxalic and methanesulphonic acids.

The salts may be obtained by conventional procedures, e.g. by mixing solutions containing equimolar amounts of the free base and desired acid, and the required salt is collected by filtration, if insoluble, or by evaporation of the solvent.

Also included are the alkali metal salts, preparable conventionally.

The compounds of the formula (I) and their O-esters, O-ethers and pharmaceutically acceptable acid addition salts are antifungal agents, useful in combatting fungal infections in animals, including humans. For example they are useful in treating topical fungal infections in man caused by, among other organisms, species of Candida, Trichophyton, Microsporum or Epidermophyton, or in mucosal infections caused by Candida albicans (e.g thrush and vaginal candidiasis). They may also be used in the treatment of systemic fungal infections caused by, for example, Candida albicans, Cryptococcus neoformans, Aspergillus fumigatus, Coccidioides, Paracoccidioides, Histoplasma or Blastomyces.

The in vitro evaluation of the antifungal activity of the compounds can be performed by determining the minimum inhibitory concentration of the test compound at which growth of the particular microorganism in a suitable medium fails to occur. In practice, a series of agar plates, each having the test compound incorporated at a particular concentration, is inoculated with a standard culture of, for example, Candida albicans and each plate is then incubated for 48 hours at 37° C. The plates are then examined for the presence or absence of growth of the fungus and the appropriate m.i.c. value is noted. Other microorganisms used in such tests can include Cryptococcus neoformans, Aspergillus fumigatus, Trichophyton spp, Microsporum spp, Epidermophyton floccosum, Coccidioides immitis and Torulopsis glabrata.

The in vivo evaluation of the compounds can be carried out at a series of dose levels by intraperitoneal or intravenous injection or by oral administration, to mice which are inoculated with a strain of Candida albicans. Activity is based on the survival of a treated group of mice after the death of an untreated group of mice following 48 hours observation. The dose level at which the compound provides 50% protection against the lethal effect of the infection, the $PD_{50}$ in mg/kg, is noted.

For human use, the antifungal compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavoring or coloring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) will be from 0.1 to 10 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of the formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and their O-ethers, O-esters and agriculturally acceptable salts also have activity against a variety of plant pathogenic fungi, including for example various rusts, mildews and moulds, and they are, therefor, useful as agricultural fungicides for treating plants and seeds to eradicate or prevent such diseases.

The following Examples illustrate the invention. All temperatures are in °C. Ratios of solvent mixtures are by volume. Percentages are by weight unless otherwise noted.

EXAMPLE 1

1,1-Difluoro-1,2-bis-(4-fluorophenyl)-3-(1H-1,2,4-triazol-1-yl)propan-2-ol

Dimethylsulphoxide (6 ml) was added under nitrogen to a mixture of sodium hydride (60% dispersion in mineral oil, 0.087 g, 2.2 mmole) and trimethylsulphoxonium iodide (0.53 g, 2.4 mmole) over a period of 5 minutes, and the mixture was warmed at 45° C. for a further 15 minutes. The solution was cooled and 2-(4-fluorophenyl)-2,2',4'-trifluoroacetophenone (0.53 g, 2.0 mmole) in dimethylsulphoxide (5 ml) was added over five minutes. The mixture was stirred for one hour at room temperature, water (20 ml) was then added and the mixture was extracted with toluene (3×25 ml). The combined toluene extracts were washed with water (2×20 ml), dried over $MgSO_4$ and evaporated to yield the epoxide (II, $R=R^1=4-FC_6H_4$) as a colorless oil (0.53 g). 1,2,4-Triazole (0.5 g, 7.2 mmole), anhydrous potassium carbonate (1.0 g, 7.2 mmole) and dry N,N-dimethylformamide (10 ml) were added and the mixture was heated at 50° C. for 90 minutes. The solvent was then evaporated under reduced pressure and the product taken up in water (20 ml). The aqueous solution was extracted with methylene chloride (3×30 ml) and the combined organic extracts were washed with water (15 ml), dried over $MgSO_4$ and evaporated to yield a colorless oil (0.67 g) which was chromatographed on silica eluting with ethyl acetate. Recrystallization of the product from a mixture of methylene chloride and petroleum ether (b.p. 60°–80° C.) gave the title compound (0.3 g, 44%). M.p. 128°–130° C. M/e 352 (M+1). Found: C, 58.22; H, 3.57; N, 11.71. $C_{17}H_{13}F_4N_3O$ requires: C, 58.12; H, 3.73; N, 11.96%.

EXAMPLE 2

1-Chloro-2-(2,4-difluorophenyl)-1,1-difluoro-3-(1H-1,2,4-triazol-1-yl)propan-2-ol Sodium hydride (50% suspension in mineral oil, 195 mg) was washed with a little dry diethylether under nitrogen and then dimethylsulphoxide (8 ml) and trimethylsulphoxonium iodide (850 mg) were added and the mixture warmed to 60° C. until evolution of hydrogen ceased (1 hour). Dry tetrahydrofuran (8 ml) was added and the mixture cooled to −40° C. 2-Chloro-2,2,2',4'-tetrafluoroacetophenone (835 mg) was added and the mixture was stirred at −40° C. for 15 minutes, allowed to warm to 10° C. over 1 hour and poured onto ice (100 g). The resulting mixture was extracted with diethylether (3×20 ml), the ether extracts 3 washed with brine (2×10 ml), dried over $MgSO_4$ and evaporated to yield the crude epoxide as a viscous oil. 1,2,4-Triazole (400 mg), anhydrous potassium carbonate (400 mg) and dry tetrahydrofuran (10 ml) were added and the mixture was heated under reflux for 18 hours. The solvent was evaporated and the residue extracted with ethyl acetate, filtered and evaporated. The product was chromatographed on silica eluting with methylene chloride containing 2% (by volume) of isopropanol and a trace of ammonium hydroxide, to give a colorless solid (210 mg) which was recrystallized from cyclohexane to give the title product as colorless crystals (0.15 g). M.p. 103°–105° C. Found: C, 43.0; H, 2.7; N, 13.4. $C_{11}H_8ClF_4N_3O$ requires: C, 42.7; H, 2.6; N, 13.6%.

EXAMPLE 3

1,1-Difluoro-2-(difluorophenyl)-3-(1H-1,2,4-triazol-1-yl)propan-2-ol

The general procedures of Examples 1 and 2 were followed but starting with 2,2,2',4'-tetrafluoroacetophenone (1.6 g) to provide the title product (0.53 g), m.p. 122° C. Found: C,48.1; H,3.4; N,15.0. $C_{11}H_9F_4N_3O$ requires C,48.0; H,3.3; N,15.3%.

EXAMPLE 4

1,1-Difluoro-2-(2,4-difluorophenyl)-1-(1-methyl tetrazol-5-yl)-3-(1H-1,2,4-triazol-1-yl)-propan-2-ol Dimethylsulphoxide (2 ml) was added dropwise under nitrogen to a mixture of sodium hydride (60% dispersion in mineral oil, 0.021 g, 0.52 mmole) and trimethylsulphoxonium iodide (0.125 g, 0.57 mmole). When effervescence ceased, dry tetrahydrofuran (4 ml) was added, the solution cooled to −10° C., and a solution of 2,2-difluoro-2-(1-methyltetrazol-5-yl)-2',4'-difluoroacetophenone (0.13 g, 0.47 mmole) in dry tetrahydrofuran (2 ml) was added. The mixture was stirred and allowed to warm gradually to 10° C. over 30 minutes.

1,2,4-Triazole (0.1 g, 1.45 mmole) and anhydrous potassium carbonate (0.1 g, 0.72 mmole) were added and the mixture was heated at 70° C. for 1 hour. The solvent was evaporated under reduced pressure and the product taken up in water (5 ml) and extracted with ethyl acetate (2×10 ml). The combined organic extracts were washed with water (3 ml), dried over magnesium sulphate and evaporated to yield the crude product as a pale yellow oil. Chromatography on silica eluting with a mixture of methylenechloride, methanol and concentrated ammonium hydroxide (93:7:1) followed by further chromatography eluting with ethyl acetate gave a white solid which was recrystallised from a mixture of ethyl acetate and petroleum ether (b.p. 60°–80° C.) to give the title compound (18 mg). m.p. 160°–165° C. M/e 358 (M+1). Found: C,43.68; H,3.14; N,27.74. $C_{13}H_{11}N_7OF_4$ requires C,43.70; H,3.10; N,27.44%.

EXAMPLE 5

The following illustrate pharmaceutical compositions for the treatment of fungal infections (a) Capsule: 71 parts by weight of the compound of Example 1 are granulated with 3 parts maize starch and 22 parts lactose and then a further 3 parts maize starch and 1 part magnesium stearate are added. The mixture is regranulated and filled into hard gelatin capsules.

(b) Cream: 2 parts by weight of the compound of Example 1 are dissolved in 10 parts of propylene glycol and mixed into 88 parts of a vanishing cream base.

(c) Pessary: 2 parts by weight of the compound of Example 2 are suspended in 98 parts of a warm liquified suppository base which is poured into moulds and allowed to solidify.

PREPARATION A 2-(4-Fluorophenyl)-2,2,4'-trifluoroacetophenone alpha,alpha-Difluoro-4-fluorophenylacetic acid [1.0 g, prepared from 4-fluorobromobenzene according to the method of Middleton and Bingham, *J. Org. Chem.*, 45, 2883 (1980)] was stirred under nitrogen with thionyl chloride (0.69 g) and dry N,N-dimethylformamide (0.036 g) at room temperature for 15 minutes and then at 70°–75° C. for one hour. The solution was cooled in ice and N,O-dimethylhydroxylamine hydrochloride (0.62 g), dry pyridine (1.5 g) and methylene chloride (15 ml) were added and the mixture stirred at 0° C. for 20 minutes and at room temperature for a further 30 minutes. Water (10 ml) was added and the methylene chloride layer separated. The aqueous phase was extracted with methylene chloride (2×20 ml) and the combined organic extracts were dried over $MgSO_4$ and evaporated. The residue was chromatographed on silica, eluting with methylene chloride to give N-methoxy-N-methyl-alpha,alpha-difluoro-4-fluorophenyl acetamide (1.13 g).

The product was taken up in dry tetrahydrofuran (25 ml), cooled to −80° C. and treated with the Grignard reagent prepared from p-fluorobromobenzene (0.9 g) and magnesium turnings (0.2 g) in dry diethylether (10 ml), with vigorous stirring under nitrogen.

The solution was allowed to warm to room temperature and allowed to stand overnight. A solution of ammonium chloride (2 g) in water (20 ml) was then added and the mixture extracted with diethylether (3×30 ml). The combined ethereal extracts were dried over $MgSO_4$ and evaporated. The crude product was chromatographed on silica eluting with a mixture of methylene chloride and hexane (1:3) to give the title compound (0.6 g, 48%). M/e 268.

PREPARATION B

2-Chloro-2,2,2',4'-tetrafluoroacetophenone

Bromo-2,4-difluorobenzene (10 g) was added to magnesium turnings (1.5 g) in dry diethylether (100 ml). The clear solution of the Grignard reagent was then added dropwise to a solution of chlorodifluoroacetic anhydride (10 g) in dry diethylether (50 ml) while stirring at −72° C. under nitrogen. After 15 minutes the reaction mixture was allowed to warm to −10° C. over one hour and then poured onto a mixture of ice (200 g) and 2N hydrochloric acid (50 ml). The mixture was extracted with diethyl ether (3×100 ml), the ether extracts dried over $MgSO_4$ and evaporated to a yellow oil which was distilled to give the title product as a colorless oil (3.6 g). B.p. 50°–80° C., 14 mm Hg.

PREPARATION C 2,2-Difluoro-2-(1-methyl-tetrazol-5-yl)-2',4'-difluoroacetophenone 1. 2,4-Difluorobenzaldehyde 2,4-Difluorobromobenzene (18.5 g) was added to dry diethyl ether (150 ml), cooled to −75° C. and n-butyllithium (61 5 ml of a 1.55 molar solution in hexane) was added under dry nitrogen over a period of 45 minutes. The mixture was stirred at −70° C. for a further 20 minutes and dry dimethylformamide (7.65 g) was added in dry diethyl ether (30 ml) at −70° C. over a period of 30 minutes. The mixture was stirred for 40 minutes and allowed to warm to −50° C. over a further 15 minutes. A solution of ammonium chloride (30 g) in water (100 ml) was added and the ether layer separated. The aqueous layer was further extracted with diethyl ether (2×50 ml) and the combined ethereal extracts were dried and evaporated to yield a pale yellow oil which was distilled at the water pump to give the desired product (13.0 g) b.p. 52°–55° C. at 14 mm Hg.

2. α-Trimethylsilyloxy-2,4-difluorobenzyl cyanide

A mixture of 2,4-difluorobenzaldehyde (13.0 g) trimethylsilyl nitrile (10.0 g) and anhydrous zinc iodide (0.6 g) was stirred at room temperature under nitrogen for 2 days. Further trimethylsilyl nitrile (4 g) and zinc iodide (0.2 g) were added and the mixture stirred for 18 hours when more trimethylsilyl nitrile (4 g) and zinc iodide (0.2 g) were added. The reaction mixture was stirred for a further 18 hours when the reaction was shown by NMR to be substantially complete. The mixture was distilled at the water pump to give the product as a pale yellow liquid (10 g, b.p. 118°–119° C., 14 mm Hg).

3. 2-(1-Methyl-tetrazol-5-yl)-2',4'-difluoroacetophenone

N-Butyllithium (10 ml of a 1.6 molar solution in hexane) was added slowly under nitrogen to a solution of dry diisopropylamine (1.63 g) in dry tetrahydrofuran (30 ml) at −10° to −15° C. The mixture was stirred at −10° C. for 30 minutes, cooled to −75° C. and a solution of the product from (2) (3.68 g) in tetrahydrofuran (20 ml) was added over 10 minutes. The mixture was stirred at −75° C. for 30 minutes and a solution of 5-chloromethyl-1-methyl-tetrazole (2.0 g) in dry tetrahydrofuran (20 ml) was added over 30 minutes, the temperature being maintained between −75° and −70° C. The mixture was stirred at −75° C. for a further 50 minutes, allowed to warm to room temperature over 45 minutes and stirred at room temperature for a further 30 minutes. Hydrochloric acid (36 ml 2N) was added and the mixture stirred at room temperature for 18 hours. The solution was then extracted with diethyl ether (2×100 ml), the extracts dried over magnesium sulphate and evaporated. Unreacted 5-chloromethyl-1-methyltetrazole was removed by distillation at 160° C. and 0.4 mm Hg to give a crude residue containing the desired product (1.9 g) contaminated with some 30% of unreacted 5-chloromethyl-1-methyltetrazole which was used directly for the next stage.

4. 2,2-Difluoro-2-(1-methyl-tetrazol-5-yl)-2',4'-difluoroacetophenone

Sodium hydride (60 mg, 60% dispersion in oil) was added at room temperature to a solution of the product from stage 3 (0.35 g) in dry tetrahydrofuran (25 ml) under dry nitrogen. When effervescence had ceased the mixture was exposed to an atmosphere of perchlorylfluoride until no more was absorbed (30 minutes). The solvent was evaporated under vacuum and the residue extracted with dry diethyl ether.

The ether solution was decanted and evaporated to give an oil. The treatment with sodium hydride and exposure to perchloroylfluoride was repeated. The product was again evaporated, extracted into diethyl ether and evaporated to yield an oil which was chromatographed on silica eluting with a mixture of hexane and ethyl acetate to yield the desired product (0.13 g). M/e 275 (M+1).

We claim:

1. A compound of the formula

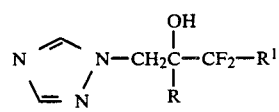

or a pharmaceutically acceptable acid addition salt thereof, wherein R is fluorophenyl or difluorophenyl, and $R^1$ is H, Cl, 1-methyltetrazol-5-yl or fluorophenyl.

2. A compound according to claim 1 wherein R is 4-fluorophenyl or 2,4-difluorophenyl and $R^1$ is H, Cl or fluorophenyl and $R^1$ is H, Cl or flyrorophenyl.

3. The compound according to claim 2: 1,1-difluoro-1,2-bis(4-fluorophenyl)-3-(1H-1,2,4-triazol-1-yl)propan-2-ol.

4. The compound according to claim 2: 1-chloro-2-(2,4-difluorophenyl)-1,1-difluoro-3-(1H-1,2,4-triazol-1-yl)propan-2-ol.

5. The compound according to claim 2: 1,1-difluoro-2-(2,4-difluorophenyl)-3-(1H-1,2,4-triazol-1-yl)propan-2-ol.

6. A compound according to claim 1 wherein R is fluorophenyl or difluorophenyl and $R^1$ is 1-methyltetrazol-5-yl.

7. The compound according to claim 6: 1,1-difluoro-2-(2,4-difluorophenyl)-1-(1-methyltetrazol-5-yl)-3-(1H-1,2,4-triazol-1-yl)-propan-2-ol.

8. A pharmaceutical composition comprising an antifungal amount of a compound or pharmaceutically acceptable salt according to claim 1 and a pharmaceutically accptable diluent or carrier.

9. A method of treating a fungal infection in an animal in need of such treatment which comprises administration to said animal an antifungal amount of a compound or pharmaceutically acceptable salt according to claim 1.